United States Patent [19]

Emerson

[11] Patent Number: 4,846,803
[45] Date of Patent: Jul. 11, 1989

[54] HYPODERMIC NEEDLE-CAP HANDLING DEVICE

[76] Inventor: Debora L. Emerson, P.O. Box 1642, Grafton, Va. 23692

[21] Appl. No.: 142,160

[22] Filed: Jan. 11, 1988

[51] Int. Cl.$^4$ ............................................. A61M 5/325
[52] U.S. Cl. .................................... 604/263; 604/192; 248/231.7; 248/316.7; 206/365
[58] Field of Search .............. 604/110, 181, 187, 192, 604/263; 206/364–366, 571; 248/231.7, 314, 316.1, 316.7

[56] References Cited

U.S. PATENT DOCUMENTS

| | | | |
|---|---|---|---|
| 2,463,400 | 3/1949 | Lowe | 248/316.7 |
| 3,494,201 | 2/1970 | Roach | 73/425.6 |
| 4,420,085 | 12/1983 | Wilson et al. | 206/571 |
| 4,596,562 | 6/1986 | Vernon | 604/263 |
| 4,623,336 | 11/1986 | Pedicano et al. | 604/192 |
| 4,629,453 | 12/1986 | Cooper | 604/192 |
| 4,717,386 | 1/1988 | Simmons | 604/263 |
| 4,737,149 | 4/1988 | Gillilan | 604/263 |
| 4,742,910 | 5/1988 | Staebler | 206/365 |

Primary Examiner—Max Hindenburg
Attorney, Agent, or Firm—Griffin, Branigan & Butler

[57] ABSTRACT

A hypodermic needle-cap handling device (10) includes a thin rigid plate (12) having an open ended slot (24) therein and a cap holder (16) mounted on one side of plate adjacent the slot for holding a needle cap (36) that has been removed from a hypodermic needle (58) with the aid of handling device. A syringe (54) can be manipulated to move a nose 60 thereof into the slot and when the syringe is thereafter moved laterally away from the plate the needle cap, which cannot pass through the slot, is left on the cap holder. The cap can be reapplied to the needle by reversing this action. The cap holder includes an end abutment (30) against which the cap can be urged when the cap is reapplied and spring clips 38 for positively holding a cap on the cap holder. Guide members (14a and b) guide the nose of the hypodermic syringe into the slot and a clamp 20 clamps the hypodermic needle-cap handling device to a table.

12 Claims, 1 Drawing Sheet

HYPODERMIC NEEDLE-CAP HANDLING DEVICE

BACKGROUND OF THE INVENTION

This invention relates broadly to the art of hypodermic needles and more specifically to a device for protecting technicians using hypodermic needles from accidentally sticking themselves with the needles.

A continuous problem for those using hypodermic needles, especially those using them often, such as nurses and the like, is that they sometimes "stick" penetrate the skin) themselves. Although such "sticking" can be a nuisance, under some circumstances it is deadly. For example, if one should stick his finger with a hypodermic needle which has previously been inserted into a patient having a deadly, blood-transmitted, disease it could mean death. In this regard, technicians working in laboratories are often handling syringes having deadly test samples therein for use with laboratory animals and the like. Disposable syringes normally come with caps on the needles thereof. These caps are normally removed by a technician by gripping the cap with one hand and the syringe with the other and pulling them apart. The cap is normally placed on a work surface while the technician utilizes the syringe to give a shot, transfer serum etc. and after the technician is through using the syringe both hands are again used to apply the cap to the needle. Thereafter, the syringe is normally discarded with the cap thereon. A critical step in this procedure is reapplying the cap to the needle because the technician is most likely to be stuck during this step. A number of suggestions have been made for preventing technicians from sticking themselves, most of them involving special needle caps having lateral-guards built thereon. Several such devices are described in U.S. Pat. Nos. 4,629,453 to Cooper and 4,623,336 to Pedicano et al. Although these caps, having laterally extending guards, do help protect technicians, they are somewhat bulky, making them difficult to store. Further, th laterally extending guards sometimes come into contact with other things, inadvertently knocking them from the needles. Also, such special caps still require users to use both hands for removing and reapplying them which involves wasted motion. It is an object of this invention to provide a device allowing easy and safe removal and reapplication of needle caps from and to hypodermic needle assemblies with reduced possibilities of users sticking themselves.

Other difficulties with needle caps having guards, and caps in general, is that when they are not in use, they tend to become mislaid and sometimes technicians must later spend valuable time looking for them. Also, although caps with guards thereon help protect technicians, they are not foolproof in that needles can still slip off the guards and inadvertently penetrate technicians. Thus, it is an object of this invention to provide a device allowing the removal and application of hypodermic needle caps which tends to prevent such caps from becoming lost and which provides a virtually foolproof means of applying caps to needles without users thereof sticking themselves.

Further, it is an object of this invention to provide a hypodermic needle-cap handling device which is inexpensive to manufacture but yet which is durable, autoclavable and extremely effective in operation.

SUMMARY

According to principles of this invention, a hypodermic needle-cap handling device comprises a thin rigid plate having an open ended slot therein and a cap holder mounted on one side thereof, adjacent the slot, for holding a needle cap that has been removed. A syringe can be manipulated to move its nose into the plate slot, with the syringe on one side of the plate and the cap on the other. When the syringe is pulled laterally away from the plate, the cap, which cannot pass through the slot, is pulled from the hypodermic needle assembly and left on the cap holder. In one embodiment the cap holder has an abutment at an outer end so that when the needle of the needle assembly is reinserted into the cap the cap impinges on the abutment to allow one to firmly seat the nose of the needle assembly in the cap. A spring clip is also included for positively holding the cap in place on the cap holder and a V-shaped guide member is used for guiding the nose of the hypodermic needle assembly into the plate slot. The handling device includes a clamp so that it can be clamped to a work surface.

BRIEF DESCRIPTION OF THE DRAWING

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF THE PREFERRED EMBODIMENT

Figure 1:
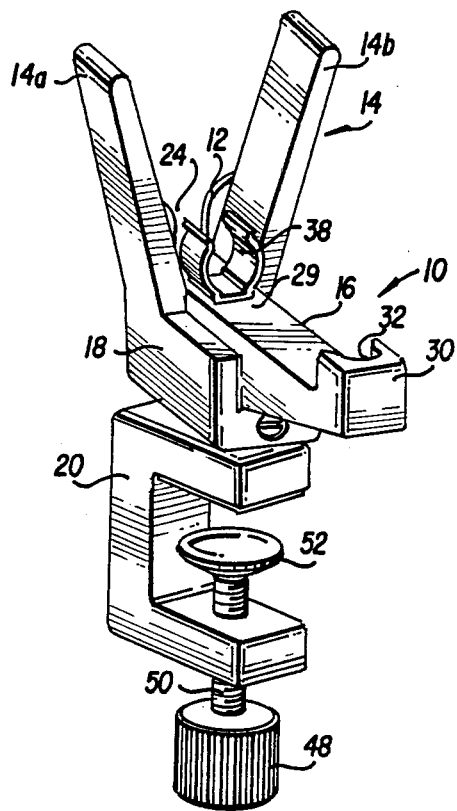
FIG. 1 is an front isometric view of a hypodermic needle-cap handling device of this invention.

A hypodermic needle-cap handling device 10 includes an approximately 1/32 stainless steel plate 12, a V-shaped large guide 14, a cap holder 16, a base 18, a clamp 20, and a swivel mount 22.

The stainless steel plate 12 defines an open ended slot 24 having diverging tapers 26 at a mouth thereof and having a breadth 28 at a lower end thereof of approximately ⅜ of an inch. The plate 12 is shown in the drawings as being screwed to large-guide members 14a and b and the base 18 at the crotch formed by the V-shaped large guide 14. The slot 24 is aligned with the V-shaped guide 14 such that the diverging tapers 26 at the mouth of the slot face the same direction as the diverging guide members 14a and b.

Figure 2:
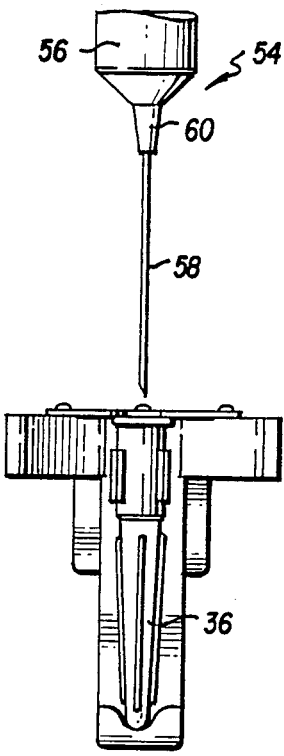
FIG. 2 is a top view of the handling device of FIG. 1 with a needle cap mounted therein and a hypodermic needle assembly shown removed from the needle cap.
Figure 3:
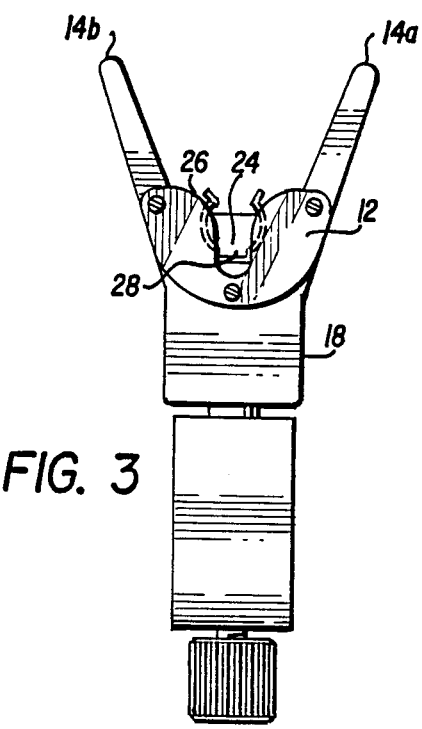
FIG. 3 is a rear view of the handling device of FIGS. 1 and 2.
Figure 4:
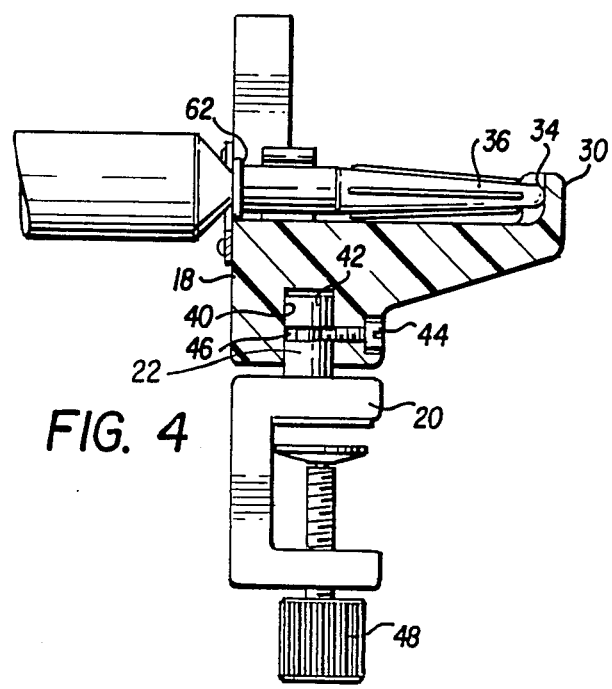
FIG. 4 is a side, partially sectional, view of the handling device of the other drawings with a hypodermic needle assembly having a cap mounted thereon located in a cap removing position.

The cap holder 16, the base 18, and the V-shaped guide members 14a and 14b are all formed of one solid piece of stainless steel. The cap holder 16 extends laterally outwardly from the plate 12 with a supporting surface 30 extending lateral to the plate 12 at the lower end of the plate slot 24. Located at an outer end of the cap holder 16 is an abutment 30 having an upwardly-open dimple 32 therein. The distance from the abutment 30 to the plate 12 is approximately the length of a needle cap with which this invention is to be used. The dimple 32 has a shape and size to approximately fit an end 34 of a needle cap 36 as is shown in FIGS. 2 and 4.

Opposing C-clamp spring clips 38 are mounted on the support surface 29 of the cap holder 16 for gripping needle caps supported by the cap holder 16 and preventing them from falling out. In some cases the spring clips 38 are not necessary, however, they allow the handling device 10 to be used in any attitude.

The base 18 has a bore 40 in the lower end thereof for receiving a slotted stud 42 mounted on the clamp 20. The slotted stud 42 allows the base 18 to swivel thereon as is depicted in FIG. 1. A screw 44 engaged in a threaded hole in the base 18 extends into an annular slot 46 of the slotted stud 42 for insuring that the base 18 does not come off of the slotted stud 42. A knob 48 is used to move a threaded shaft 50 in a threaded bore (not shown) in the clamp 20 to move a clamping member 52 for clamping the clamp 20 to a table surface.

In operation, the C clamp 20 is clamped to a table surface and the base 18 is swiveled on the slotted stud 42 so that a user is positioned to the rear of the handling device (on the side of the large guide 14 opposite the cap holder 16). When the user is ready to use a hypodermic needle assembly 54 having a syringe 56 with a needle 58 mounted on a nose 60 thereof he will remove the same from a package and at that time it will have a needle cap 36 friction fitted onto the nose 60 to cover the needle 58. The user holds the syringe 56 and manipulates therewith the nose 60 down between the guide members 14a and 14b of the large guide 14 until the nose 60 comes into contact with the diverging tapers 26 of the plate 12. The users continues to move the syringe downwardly and the nose 60 is guided into the slot 24 of the plate 12, with the needle cap 36 being on the cap holder 16 side of the plate 12 and the syringe 56 being on the opposite side of the plate 12. As the needle cap 36 is moved downwardly, it forces the spring clips open and moves therebetween. Finally, the needle cap 36 comes into contact with the support surface 29 of the cap holder 16 and the user then stops urging the syringe 56 downwardly. The user now pulls the syringe outwardly, away from the handling device 10. The needle cap 36 is prevented from following the syringe by the plate 12 since a small flange 62 at the inner end of the needle cap 36 is too large to pass through the slot 24. Thus, the needle cap 36 is separated from the syringe 56 as is depicted in FIG. 2 and is left positively held on the support surface 29 by the spring clips 38. The user then utilizes the hypodermic needle assembly 54 and when he is finished he reverses this action by inserting the needle 58 into the needle cap 36 through the plate slot 24. As he does this, the abutment 34 impinges on the outer end of the needle cap 36 to allow the user to firmly drive the syringe nose 60 into the needle cap 36 so that it is firmly held thereto by friction. Simultaneously, or immediately following, the user lifts upwardly on the syringe 56 to remove the needle cap 36 from the handling device 10 and he thereafter discards the hypodermic needle assembly 54 with the needle cap 36 mounted thereon.

It will be understood by those skilled in the art that with this invention a user can remove a needle cap and then reapply it with one hand and at absolutely no risk to himself. Further, with this invention, when a needle cap is not in use it is maintained in one specific spot so that the user has no trouble finding it once he or she is ready to reapply it to the hypodermic needle assembly. The device is relatively uncomplicated and easy to use.

While the invention has been particularly shown and described with reference to a preferred embodiment, it will be understood by those skilled in the art that various changes in form and detail may be made therein without departing from the spirit and scope of the invention. For example, the clamp 20 is not necessary to the invention, however, it makes the invention extremely practical and easier to use. It would also be possible to make the handling device much thinner than shown in the drawings. For example, it would be possible to make the base 18 and large guide 14 of sheet-like stainless steel as well as the cover holder. In such an embodiment the large guide 14 and the plate 12 could be one member.

Further, it is possible to make the various parts in various other manners than those described herein. For example, it is not necessary that the base 18, the large guide 14 and the cap holder 16 all be formed from one piece.

The embodiments of the invention in which an exclusive property or privilege are claimed are defined as follows:

1. A hypodermic needle-cap handling device for aiding in the removal and reapplication of a cap from and to a hypodermic needle of a hypodermic needle assembly, said hypodermic needle assembly being of a type having a needle attached to a nose of a syringe, said cap, which has a cavity for receiving the needle in a mouth thereof, being attachable to said hypodermic needle assembly by means of friction, said handling device comprising:
   a thin rigid plate having a slot therein with one end of said slot forming an open mouth, said slot having a width which is larger than said nose of said hypodermic syringe but which is narrower than the width of said cap;
   a cap holder mounted on one side of said rigid plate adjacent said slot for holding a needle cap that has been removed from a hypodermic needle assembly with the aid of said handling device, said cap holder having a surface extending laterally to said thin rigid plate for holding said needle cap with its cavity mouth being directed towards said slot;
   whereby a syringe of a hypodermic needle assembly having a cap thereon, can be manipulated to move its nose into said slot of said thin rigid plate with the syringe on one side and the cap on the other side of the plate, said syringe can then be pulled laterally away from said thin rigid sheet while said cap, which cannot pass through the slot, is pulled from the hypodermic needle assembly and left on the cap holder; thereafter, the syringe can be manipulated to pass the needle again through the slot into the cavity mouth of the needle cap to reapply the needle cap to the hypodermic needle assembly.

2. A handling device as in claim 1 wherein said cap holder includes an abutment on an end thereof away from said rigid plate for impinging on an outer end tip of a needle cap when said needle cap is reapplied with said handling device.

3. A handling device as in claim 2 wherein is further included a spring clip means mounted on said cap holder for positively holding a needle cap supported by said cap holder.

4. A handling device as in claim 3 wherein said thin rigid plate is mounted on a larger member forming V-shaped guides for guiding a hypodermic syringe into the open mouth of said slot.

5. A handling device as in claim 4 wherein said handling device includes a clamp for clamping said handling device to a work surface.

6. A handling device as in claim 1 wherein is further included a spring clip means mounted on said cap holder for positively holding a needle cap supported by said cap holder.

7. A handling device as in claim 6 wherein said thin rigid plate is mounted on a larger member forming V-shaped guides for guiding a hypodermic syringe into the open mouth of said slot.

8. A handling device as in claim 7 wherein said handling device includes a clamp for clamping said handling device to a work surface.

9. A handling device as in claim 1 wherein said thin rigid plate is mounted on a larger member forming V-shaped guides for guiding a hypodermic syringe into the open mouth of said slot.

10. A handling device as in claim 9 wherein said handling device includes a clamp for clamping said handling device to a work surface.

11. A handling device as in claim 10 wherein said cap holder includes an abutment on an end thereof away from said rigid plate for impinging on an outer end tip of a needle cap when said needle cap is reapplied with said handling device.

12. A handling device as in claim 1 wherein said handling device includes a clamp for clamping said handling device to a work surface.

* * * * *